United States Patent [19]

Rao et al.

[11] 4,259,868

[45] Apr. 7, 1981

[54] METHOD AND APPARATUS FOR NONDESTRUCTIVE TESTING OF CEMENT

[75] Inventors: Prabhakar P. Rao; David L. Sutton, both of Duncan, Okla.

[73] Assignee: Halliburton Company, Duncan, Okla.

[21] Appl. No.: 80,827

[22] Filed: Oct. 1, 1979

[51] Int. Cl.[3] .......................................... G01N 29/00
[52] U.S. Cl. ................................................. 73/597
[58] Field of Search ................. 73/597, 594, 590, 803

[56] References Cited

U.S. PATENT DOCUMENTS 3,504,532  4/1970  Muenow et al. .................. 73/597

FOREIGN PATENT DOCUMENTS

306412  8/1971  U.S.S.R. ................................. 73/597
386332  9/1973  U.S.S.R. ................................. 73/597
566177  9/1977  U.S.S.R. ................................. 73/597

Primary Examiner—Anthony V. Ciarlante
Attorney, Agent, or Firm—John H. Tregoning; William J. Beard

[57] ABSTRACT

Methods and apparatus for the nondestructive testing of cement slurry samples as a function of time are disclosed. A sample placed in a temperature and pressure controlled autoclave is coupled to transducer means under computer control. Ultrasonic energy is propagated through the sample and the transit time is measured. A predetermined relationship relating transit time to compressive strength is employed and enables the determination of compressive strength. The measurements are repetitively performed on up to eight samples simultaneously and the time history of the development of compressive strength is recorded.

25 Claims, 8 Drawing Figures

METHOD AND APPARATUS FOR NONDESTRUCTIVE TESTING OF CEMENT

BACKGROUND OF THE INVENTION

This invention relates to methods and apparatus for testing the compressive strengths of cement and cement slurry mixtures. More particularly the invention relates to non-destructive methods and apparatus for testing such cement slurries and cement samples.

Historically, in order to determine the compressive strength of cement as a function of time it has been necessary to prepare a multiplicity of samples of the cement in small test cylinders, or cubes, and to then destructively test (or crush) a series of such samples as a function of time as the cement cured. In testing batches of cement in this manner, while the cement may be cured at elevated temperatures and pressures such as are present in a wellbore environment, it has been necessary to remove the cement samples from the elevated temperature and pressure environment in order to perform the crushing test on the strength measuring machines required for this purpose. Thus the actual testing of cement samples has been performed usually at room temperature and at atmospheric pressure, rather than at the actual temperature and pressure present in a well borehole environment.

It is apparent that such prior art methods for testing the compressive strengths of cements as a function of time have many shortcomings. For example, the samples taken from a particular batch of cement to form the multiplicity of cylinders required for such testing may not be uniform. Similarly, the removal of the sample cylinders from the elevated temperature and pressure conditions for testing at atmospheric pressure and room temperature could conceivably alter the physical properties of the cement, i.e., the very properties being measured. Moreover, such testing is inconvenient, cumbersome and time consuming.

The time required for oil or gas well cementing slurry to reach an initial set and to develop useful compressive strength are important parameters in scheduling further drilling or completion operations. For example, operations such as well temperature logs to locate the top of a cement column, cement bond logs to evaluate cement jobs, the continuation of drilling after setting intermediate casing or liners, the perforating of production zones, or the clean out and well stimulation treatments after such operations as squeeze cementing, all require a knowledge of the compressive strength and initial set time of the cement slurry used in the operation.

Without reliable set time and compressive strength data, temperature logs and cement bond logs can be run to soon or delayed unnecessarily. Additional drilling in a well borehole can also be carried out either prematurely or later than needed. If well clean up and stimulation treatments are carried out too soon after a squeeze cement treatment, interzone communication problems may develop. Similarly, it has been found that well perforating during the early stages of strength development of the cement slurry around a well casing can result in cleaner perforations with less shattering and giving better zone isolation. From these examples, it may be seen that a precise knowledge of the initial set time and strength development of the cement slurry used in well completions or treatments are essential to perform the above type operations at the optimum time to avoid unnecessary delays.

BRIEF DESCRIPTION OF THE INVENTION

The present invention provides methods and apparatus for nondestructively testing samples of a cement slurry to provide information concerning the initial set time of the slurry and the development of mechanical compressive strength of the slurry as a function of time. A high temperature and pressure controlled autoclave houses a small cylindrical sample of the cement slurry to be tested and maintains elevated temperature and pressure conditions as desired on the sample throughout the testing procedure. Ultrasonic transducer elements are coupled to opposite ends of the sample in the high temperature and pressure autoclave. The transmitting transducer is pulsed periodically and the travel time of the ultrasonic signal from the transmitting transducer to the receiving transducer is measured periodically. A completely automated electronic system is provided for obtaining the travel time measurements.

When the travel time measurements are obtained, a predetermined, empirically derived relation is used which establishes the initial set time and the compressive strength of the sample as a function of the transit time of ultrasonic waves through the sample. A time record of the transit time and the computed compressive strength may be made by repeating the test continuously as a function of time. The system of the present invention is thus equipped to derive a complete history of the initial set time and compressive strength characteristics of the slurry being tested as a function of time. This information may be displayed either in graphical form or by digital readouts. The system is further adapted to make such nondestructive measurements of the cement samples strength properties on a multiplicity of cement samples simultaneously in parallel.

Other and further advantages of the present invention will become apparent from the following detailed description thereof when taken in conjunction with the accompanying drawings in which:

DESCRIPTION OF THE PREFERRED EMBODIMENT

The nondestructive testing system of the present invention is based upon measurement of the travel time of an ultrasonic signal coupled through a sample of cement or cement slurry whose characteristics are to be measured. A very accurate generalized relationship for relating the compressive strength of cement samples to the travel time of an ultrasonic energy therethrough has been developed. A technique for accurately measuring the change in transit time through a two inch cylindrical cement sample over a period of time and thereby compiling a record of its strength history is provided in the system of the present invention.

The transit time of an ultrasonic signal over a distance of two inches in a cement sample can range from 30-40 microseconds during the early stages of strength development and will decrease to about 10-12 microseconds during the final stages of strength development. Measurements of the transit time of the ultrasonic signal through the sample necessitates detecting weak signal arrivals during the initial stages of strength development. The system attempts to measure the transit time arrival of the first received peak of the ultrasonic wave transiting the sample to an accuracy of about plus or minus 30 degrees. A one percent detection resolution for a 30 microsecond transit time thus requires detecting the received ultrasonic energy pulse to an accuracy of about plus or minus 0.3 microseconds. In translating this to a detection error allowable of about plus or minus 30 degrees of the first true peak of the arrival, then 0.3 microseconds is equivalent to the use of a frequency for the ultrasonic signal of about 277 kilohertz. In order to take into account equipment timing errors and timing triggering errors, the system of the present invention uses a slightly higher ultrasonic frequency of about 400 kilohertz. This frequency has been found to give sufficient transmisibility of the ultrasonic signal to provide reliable detectability and time resolution of the arrival of the first peak, during the early stages of compressive strength development.

Moreover, such a frequency is compatible with the measurement of the initial set time of a cement slurry. For this purpose the frequency selected for use must be low enough to transmit a detectable signal through unconsolidated slurry, (i.e. wavelength short enough) to prevent undue scattering from aggregate particles in the slurry and high enough to provide the required accuracy of transit time measurements.

Figure 6:
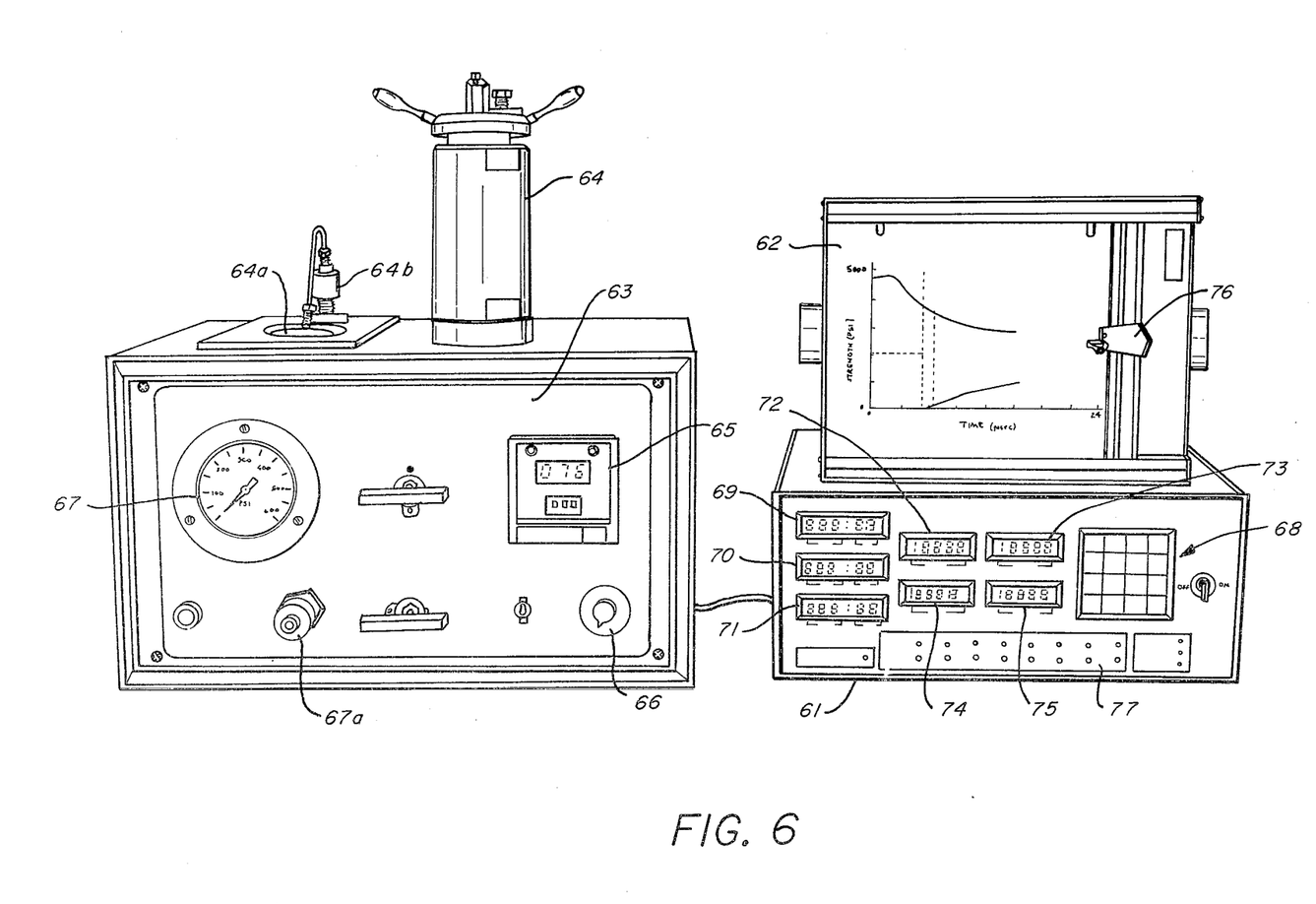
FIG. 6 is a isometric view illustrating the configuration of a cement analyzing system in accordance with the concepts of the present invention.

Referring initially to FIG. 6, the components of a cement analyzer system according to the concepts of the present invention are illustrated schematically in elevation. A control computer 61 having a multichannel capability is illustrated connected to a single measurement sample autoclave 63. The system can handle up to eight such autoclaves in parallel, simultaneously. Also connected to the control computer 61 is a digital plotter 62. The control computer 61 is provided with a keyboard 68 for entering data and command functions into the system.

The control computer is supplied with seven digital readout displays 69, 70, 71, 72, 73, 74 and 75. Display 69 is a display of the initial set time of a particular cement sample. Display 70 is a digital readout of the time required to reach an arbitrary programmable value of compressive strength, referred to as Strength 1. Similarly, digital display 71 is the time required to reach an arbitrary programmable strength value called Strength 2. Digital display 72 displays the value in psi of Strength 1. Digital display 74 is the value in psi of Strength 2. These programmable values of strength to be reached are those indicated by the timers 70 and 71. Digital display 73 shows the current average value of the compressive strength of a cement sample. Finally, digital display 75 shows the ultrasonic transit time value currently measured for a particular cement sample. The numerical values displayed at any given time refer to a particular selected channel of the system.

Panel display 77 is the channel status for any of the eight possible channels which may connected to the control computer 61. LED (light emitting diode) displays illustrate the current status of data in each channel. The particular channel which is selected has the numerical values pertaining to the sample in that channel displayed in the digital register displays previously discussed. Selection of a particular channel for display is accomplished by data entry from the keyboard 68.

The cement samples being analyzed are housed in one of the eight possible autoclaves connected to the channels of the control computer 61. A typical temperature and pressure autoclave 63 is illustrated in FIG. 6. The autoclave unit 63 is provided with a pressure vessel 64 which will contain the cement sample being analyzed and the ultrasonic transducers (not shown) which are acoustically coupled thereto during the analysis. The cement sample is placed inside pressure chamber 64 which is then inserted into an opening 64a in the top of the autoclave 63 where it is connected to the pressure line 64b. The gage 67 on the front of the autoclave panel monitors the pressure applied to the sample in the pressure chamber 64. The rate of temperature rise of the sample in the pressure chamber 64 is controlled by variable transformer control 66 on the front of the autoclave 63 which controls the current through a heater coil therein (not shown). The temperature measured at the autoclave pressure vessel itself is controlled by and displayed on a temperature control unit 65 also on the front panel of the autoclave unit 63. Pressure for pressuring up the pressure chamber 64 is supplied via an external connection 67a on the front panel of the autoclave 63. Thus, a cement or slurry sample to be analyzed is placed in the pressure vessel 64, inserted into the autoclave opening 64a and has its temperature controlled via temperature control 65 and 66. A plurality of up to eight of such autoclaves are then connected to the control computer 61 which performs continuous testing thereon.

Figure 4:
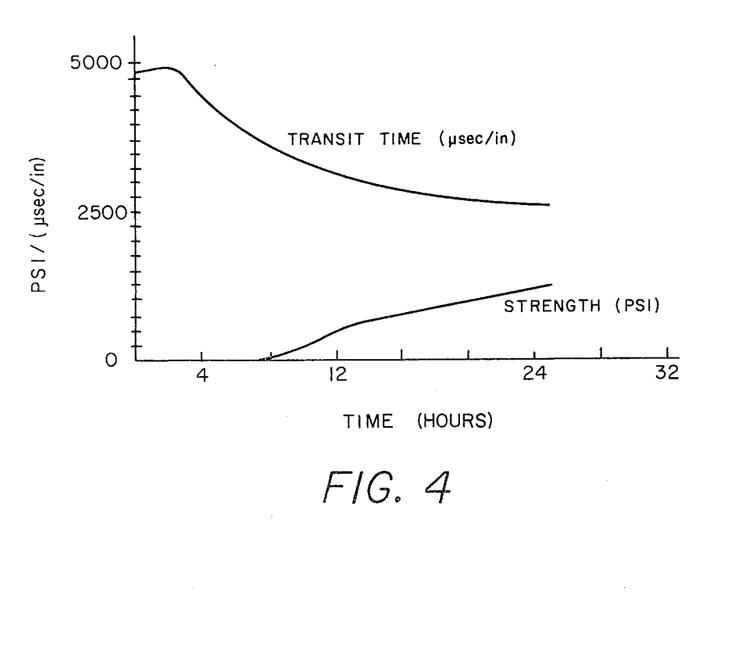
FIG. 4 is a graphical representation illustrating a typical system output of the measurement of compressive strength of a sample and transit time of ultrasonic signal therethrough, as a function of time.

The results of the testing on a particular sample may be plotted on a digital plotter 62 as illustrated in FIG. 6. A movable electromechanical pen head 76 driven by the control computer 61 may be utilized to draw the compressive strength and transit time curves as a function of time, as a test on a particular sample channel is performed. FIG. 4 illustrates in more detail a typical plot of transit time and strength of a sample as a function of time and is similar to the plot illustrated in FIG. 6 on the digital plotter 62. It can be observed in FIG. 4, for example, that as the transit time of acoustic signal across the sample decreases as a function of time, the compressive strength in psi of the sample increases. It will be appreciated that up to eight such plots could be recorded for the eight separate channels of the measurement system of the present invention.

Figure 3:
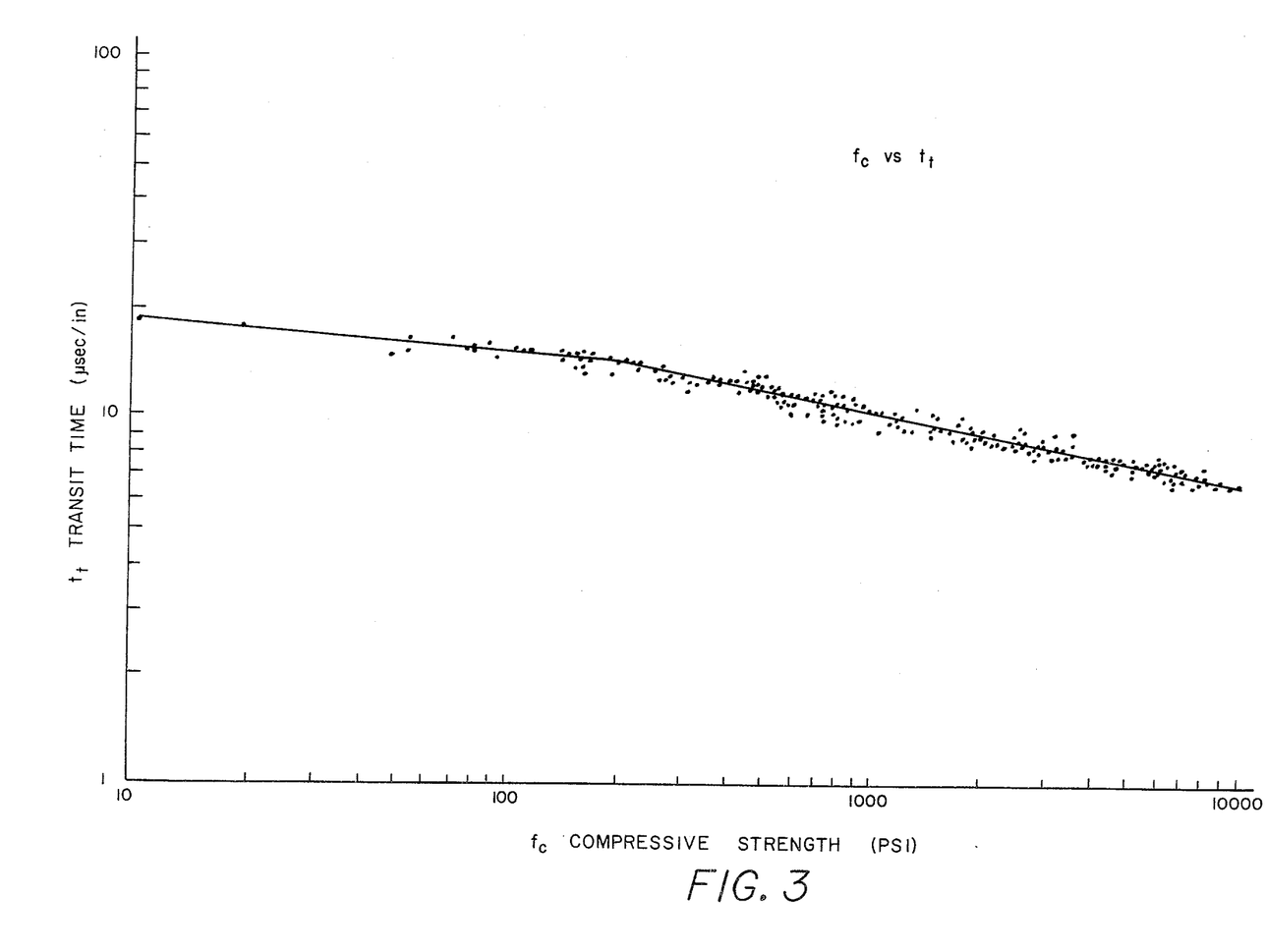
FIG. 3 is a graphical representation illustrating a generalized relationship between the compressive strength of cement samples and the transit time of ultrasonic signal therethrough.

Referring now to FIG. 3 an empirically derived graphical representation illustrating the relationship between the compressive strength in psi of cement samples as a function of the transit time of ultrasonic signal is illustrated. The curve drawn through the data points of FIG. 3 may be expressed by a mathematical equation which is accessible by the control computer of the system. The graphical representation of FIG. 3 represents the results of compressive strength measurements made on many samples of different density and chemical composition cements typical of use in oil field operations. While the generalized graphical relationship of FIG. 3 is of sufficient accuracy for use in oil field cementing applications, if more accurate results are desired, such a calibration curve for a particular type of cement can be derived and substituted therefor. It is thus seen that by deriving a graphical relationship such as that of FIG. 3, that if the transit time for an ultrasonic signal across a sample can be accurately measured that this can be related to the compressive strength of the cement as the transit time changes during the curing process.

Figure 5:
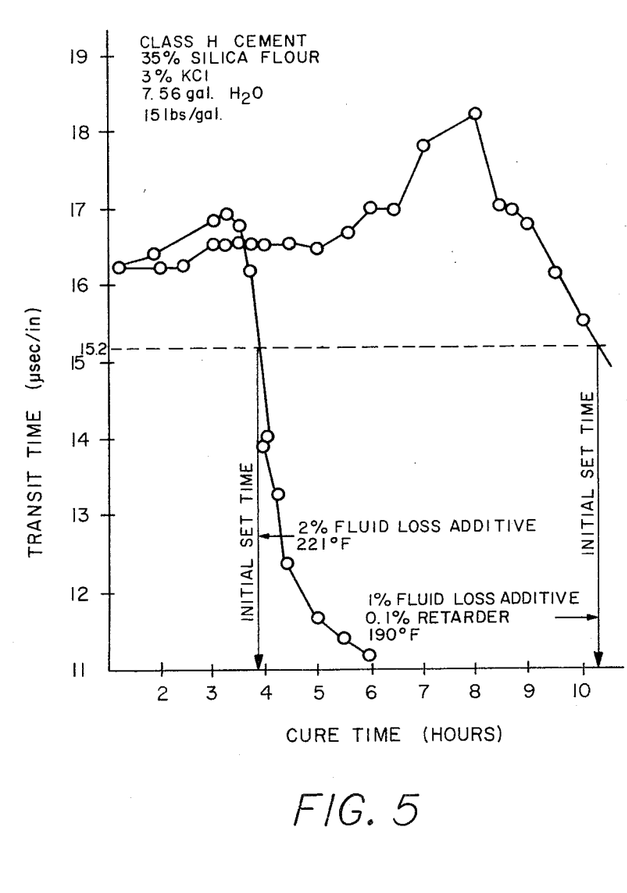
FIG. 5 is a graphical illustration depicting the variation of tansit time of an ultrasonic signal through a sample as a function of the cure time of the cement.

FIG. 5 illustrates a technique for determining the initial set time of a cement sample. The cement sample being analyzed is placed into the pressure vessel 64 of FIG. 6 in its slurry form. The initial set time of the cement slurry is defined as the time at which the slurry has solidified to a point having approximately 50 psi compressive strength. The graphical relationship of FIG. 5 illustrates the characteristics of two different types of cement typical for use in oil well applications. The samples illustrated in FIG. 5 are measured at different temperatures. The horizontal dashed line at a value of about 15.2 microseconds per inch transit time represents a value of approximately 50 psi according to the graphical relationship of FIG. 3. It can be seen in the illustration of FIG. 5 that one of the two cements tested reaches its initial set time value at about 3 hours 50 minutes from the beginning of the test. The other cement tested in the graphical relationship of FIG. 5 does not achieve this strength value until some 10 hours and fifteen minutes after the initiation of the test. In either case however, the initial set time which may be displayed on the digital display panel of the control computer 61 of FIG. 6, occurs when the slurry mixture has achieved a compressive strength of approximately 50 psi. Measurement of the value of the initial set time would have been impossible to make under controlled temperature and pressure conditions according to the techniques of the prior art. However, by use of the system of the present invention such measurements are relatively easily obtained.

Figure 1:
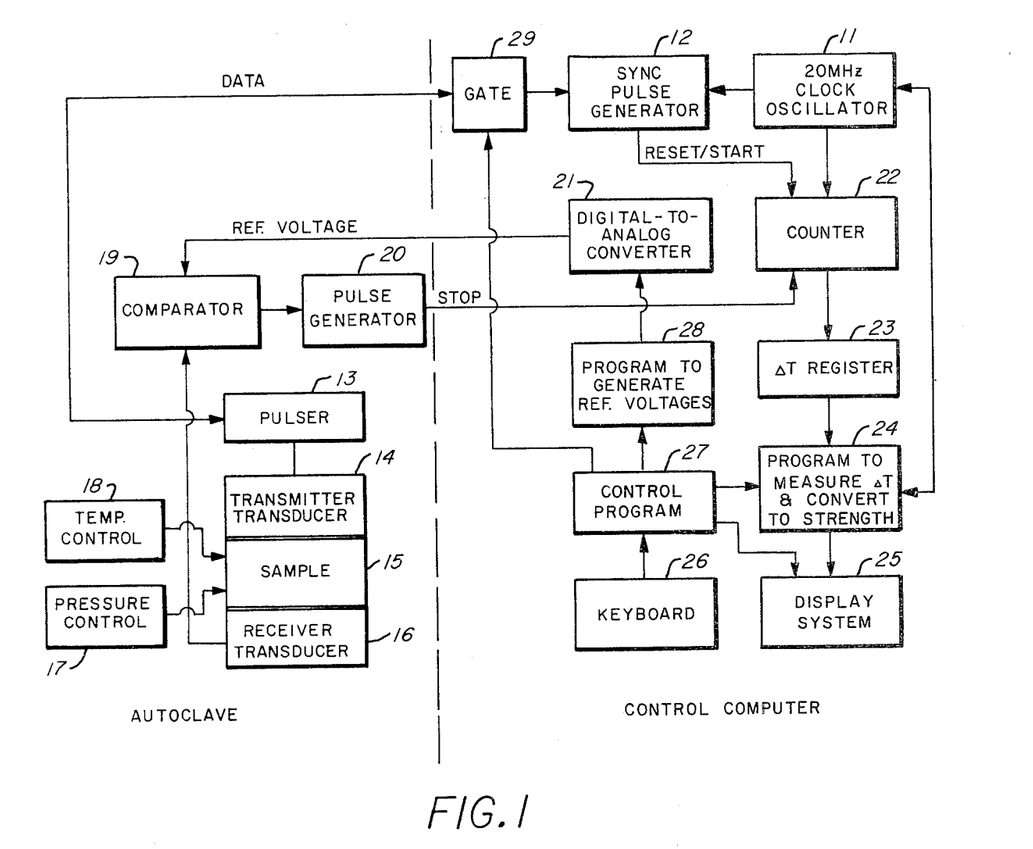
FIG. 1 is a schematic block diagram illustrating a single channel of one embodiment of a system according to the present invention.
Figure 2:
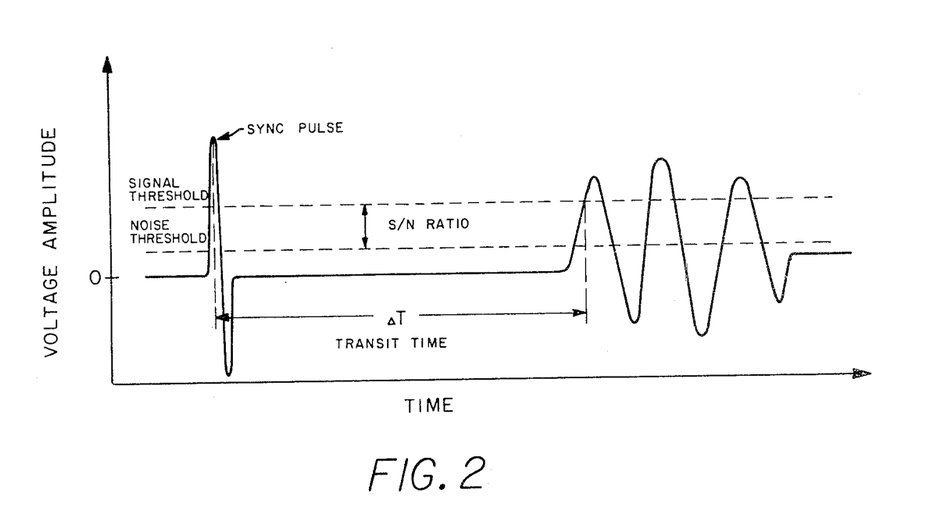
FIG. 2 is a schematic representation of a waveform showing the received acoustic signal transmitted through a cement sample.

Referring now to FIGS. 1 and 2, a measurement system for a single channel for measuring the transit time of an ultrasonic signal through a cement sample and for displaying the resultant measurement of compressive strength is illustrated schematically in block diagram form. FIG. 2 illustrates schematically a typical voltae waveform from the ultrasonic receiver transducer shown as a function of time. The system may be best understood by reference to these two figures taken in conjunction with each other.

In FIG. 1, the portion of the measurement system contained in the autoclave unit is to the left of the vertical dotted line. The portion of the measurement system in the control computer is to the right of the vertical dotted line. A sample of cement, whose strength characteristics are to be analyzed as a function of time, is acoustically coupled to a transmitter transducer 14 and to a receiver transducer 16 in the autoclave unit. These transducers comprise piezoelectric crystals having a central frequency of operation of 400 kilohertz as previously discussed. A pressure control system 17 and a temperature control system 18 of conventional design act on the sample 15 to maintain it at predetermined temperature and pressure throughout the test. When the transmitting transducer 14 is fired a signal waveform is transmitted thru a test sample and received by the receiver transducer 16. From receiver transducer 16, a signal analogous to the waveform illustrated in FIG. 2 is supplied to one input of a comparator 19. A reference voltage is supplied to an opposite input of the comparator 19 from the control computer. The reference voltage supplied to the comparator 19 is generated in digital form by a reference voltage program 28 and converted to analog form via a digital to analog converter (DAC) 21 prior to being supplied to the comparator 19. The control program which generates the reference voltage will be explained with more particularity subsequently. It will suffice to say at this point that the reference voltage supplied to the comparator 19 determines the signal threshold for detecting the signal arrival at the receiver transducer 16 from the transmitter transducer 14 after the signal has transited the sample of cement being analyzed.

In the control computer, a 20 megahertz clock oscillator 11 supplies signals to a synchronization or sync pulse generator 12, to a counter 22, and to the program 24 which measures the transit time and converts this to compressive strength for the cement sample. The sync pulse generator 12, which may comprise a divider chain or the like, supplies sync signals to the counter 22 and, via a gate 29, to a pulser 13 located in the autoclave unit. Input commands from the system operator are supplied via keyboard 26 and control program 27 to the display system 25 and the measurement program 24. These commands comprise input information as to the value of Strength 1 and Strength 2, the two programmable values of strength whose achievement will result in a time being displayed on digital display as discussed with respect to FIG. 6. Similarly, commands to change the display values from one channel to another or to change the status of a test on a given channel may be entered via the keyboard 26.

In practice, the control computer is programmed to cycle from channel to channel making measurements of the transit time of the ultrasonic signal through the sample in each channel. A complete cycle through all measurement channels is made once every ten seconds during the process. The newly measured transit time in each channel is averaged with previous values after the digital filtering during each cycle of the control computer.

In operation, at the beginning of each measurement cycle on a given channel, a noise level for the channel is established in the following manner. The measurement program 24 commands, via the reference voltage program 28, a sequence of initial reference voltages. The pulser 13 is disabled via gate 29 during this sequence. These reference voltages start at a high value and are decreased in steps until a noise threshold voltage, as illustrated in FIG. 2, is reached. At this point the comparator 19 will detect electrical noise in the system exceeding some value of the reference voltage. This establishes the noise threshold voltage. When this occurs, comparator 19 generates an output pulse to the pulse generator 20 which supplies a signal pulse to the control program 27 in the control computer. When the ambient noise level is thus established, the control program 27 enables the gate 29 to pass sync pulses from the sync pulse generator 12 to the pulser 13. On the next cycle, the sync pulse generator 12 is permitted to signal the pulser circuit 13 in the autoclave. Pulser circuit 13 pulses the transmitting transducer 14 with a voltage pulse generating ultrasonic energy from the transmitter transducer 14. The ultrasonic energy passes through the sample 15 to the receiver transducer 16. Simultaneously with signalling pulser 13, a reset/start pulse is provided to counter 22. This start pulse enables counter 22 to begin counting the 20 megahertz clock oscillator signals from the clock oscillator 11. Upon firing the pulser circuit 13, the control program 27 and measurement program 24, acting in conjunction, establish a signal detection criteria. A signal detection level voltage is established by adding a predetermined signal to noise ratio voltage to the reference voltage supplied to the comparator 19 to establish the noise reference threshold. Typically, the signal to noise ratio required for detection of a signal arrival is from 15 to about 75 db greater than the noise threshold which has just been established. Thus, when the ultrasonic signal from the transmitter 14 reaches the receiver 16, a voltage waveform similar to that of FIG. 2 is generated. The first wave arrival reaches the comparator 19. When the voltage level from the ultrasonic receiver 16 exceeds the threshold voltage supplied from the reference voltage program 28 (via DAC 21) the comparator 21 produces an output signal. The output from comparator 19 is conducted to pulse generator 20 which sends a stop pulse to the counter 22 in the Computer Unit. The stop pulse stops the counter 22 at the value of elapsed time since the firing of the acoustic transmitter transducer. The counter 22 will thus contain a binary number representative of the travel time of the acoustic wave across the sample 15. This number is strobed into $\Delta T$ register 23, and is thereby made accessible to the measurement program 24.

The measurement program 24 performs logical filtering on the travel time to assure that it is a reasonable value when compared with previously determined travel time on previous measurement cycles. The measurement program 24 then, using the equation representing the graphical relationship of FIG. 3, converts the transit time measurement to the present compressive strength of the cement sample being analyzed. This value may then be entered into the display system 25. The display system 25 keeps a running average of the last few measurements of transit time. This average is displayed via the digital readout of the front panel of the control computer, and may also be supplied to the digital plotter previously discussed with respect to FIG. 6.

Figure 7:
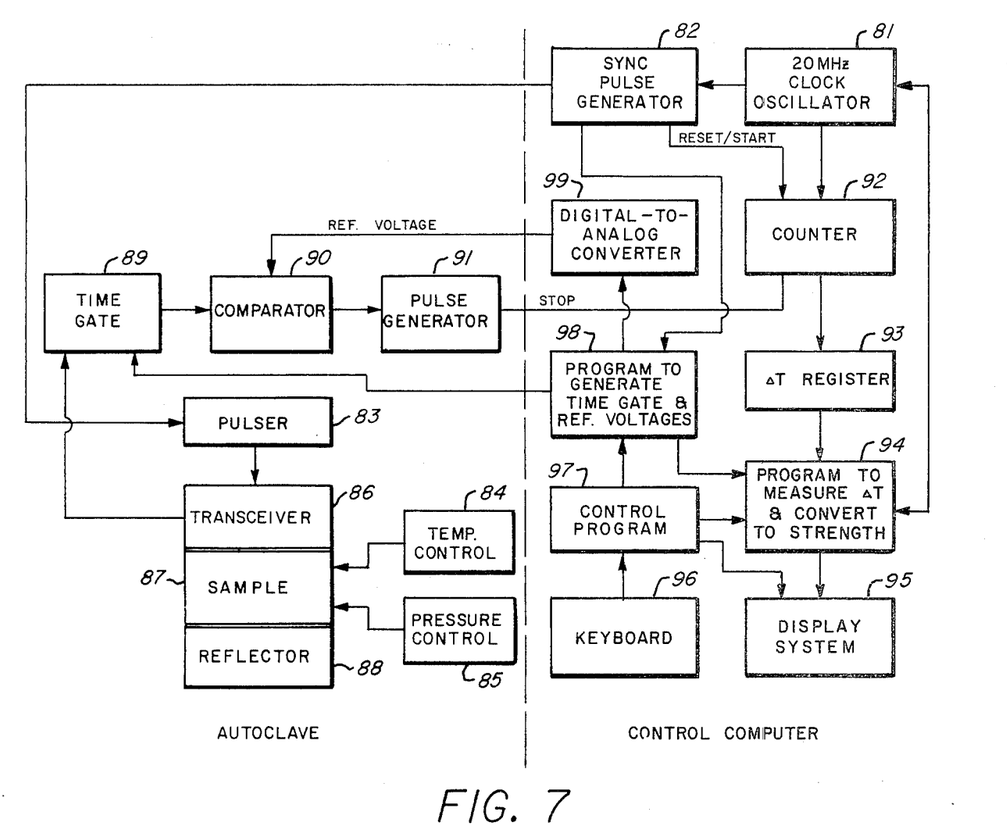
FIG. 7 is a schematic block diagram showing a single channel of an alternate embodiment of the present invention.
Figure 8:
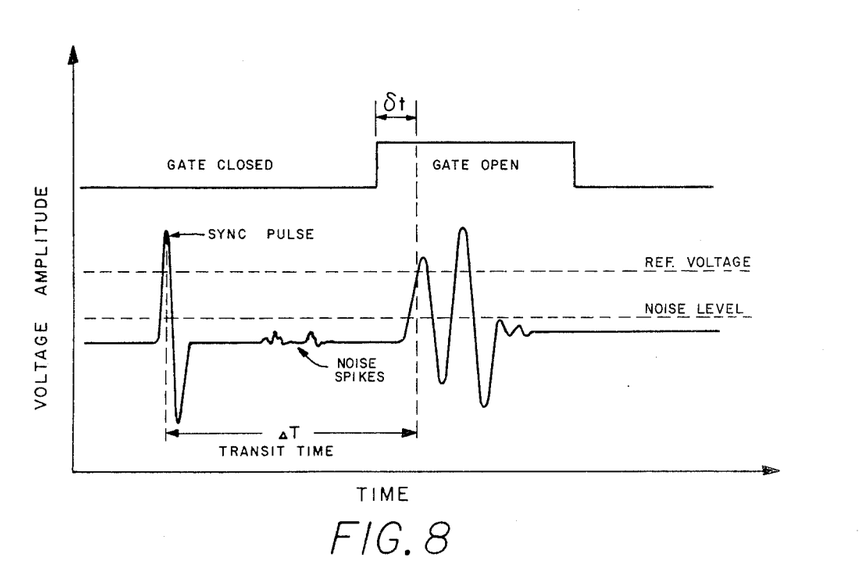
FIG. 8 is a schematic representation of a waveform showing the received acoustic signal in conjunction with the time gating arrangement of the embodiment of FIG. 7.

Referring now to FIGS. 7 and 8 an alternative arrangement of the cement analyzer of the present invention is shown in block diagram form. FIG. 8 illustrates schematically a typical voltage waveform from the ultrasonic transceiving transducer of FIG. 7 as a function of time. The system of FIG. 7 may be best understood by reference to FIGS. 7 and 8 taken in conjunction with each other.

In FIG. 7 the portion of the measurement system contained in the autoclave unit is to the left of the vertical dotted line. The portion of the measurement system in the control computer is to the right of the vertical dotted line. A cement sample 87, whose strength characteristics are to be analyzed as a function of time, is acoustically coupled to a transceiving transducer 86 in the autoclave unit. A metallic reflecting member 88 is coupled to the opposite side of the sample 87. In the embodiment of FIG. 7 the transceiving transducer 86 emits a very short duration burst of ultrasonic waves which travel through the sample 87 in a direction away from the transceiver and are reflected by the reflector 88 back through the sample 87. The reflected waves are received at the transceiving transducer 86, which at this time, is operating in receiver mode.

The transceiving transducer 86 may comprise a piezoelectric crystal having a central frequency of operation of approximately 400 kilohertz as previously discussed. A pressure control system 85 and a temperature control system 84 of conventional design act on the sample 87 to maintain it at a predetermined temperature and pressure throughout the test.

When the transceiving transducer 86 is fired to transmit a signal, the ultrasonic signal energy passes in two directions through the sample 87. After being reflected by the reflector 88 the ultrasonic signal returns to the transceiving transducer 86. The signal waveform, which is analogous to that shown in FIG. 8, is then supplied, via a timegate 89, to a comparator 90. A reference voltage is supplied to an opposite input of the comparator 90 from the control computer. The reference voltage supplied to the comparator 90 is generated in digital form by a control program 97 and a reference voltage generating program 98 in the control computer. The digital output of the reference voltage program 98 is converted to analog form via a digital to analog converter (DAC) 99 prior to being supplied to the comparator 90. The control program 97 and the program 98 which generates time gate and reference voltages will be explained in more detail subsequently. The reference voltage is determined in generated by the program 98, however, the same manner as that previously discussed with respect to FIGS. 1 and 2, so this will not be described further.

In the control computer of FIG. 7 a 20 megahertz clock oscillator 81 supplies signals to a synchronization or sync pulse generator 82, to a counter 92, and a to a program 94 which measures the transit time of the ultrasonic signal across the cement sample and converts this to a compressive strength for display. The sync pulse generator 82, which may comprise a divider chain or the like, also supplies sync pulses to the counter 92 and to a pulser 83 located in the autoclave unit. Additionally, the sync pulse generator 82 supplies sync signals to the program 98 for generating gating signals which are supplied to time gate 89 in the autoclave unit. The time gate 89 is utilized to obviate spurious noise arrivals from noise occurring in the circuitry of the autoclave unit or from possible reverbration, or ringing, of the transceiver transducer 86 from the transmitting pulse. In operation the program 98 has available to it the previous averages of the transit time values for the ultrasonic signals to transverse the sample 87 as determined by the program 95. The program 98 thus knows the approximate arrival time to be expected for the next pulsing of the transceiver transducer 86 as this value will change rather slowly as a function of time. Upon receipt of the sync pulse from the sync pulse generator 82, the program 98 then conditions the time gate 89 to open only after the passage of a predetermined length of time based upon the last transit time measurement.

This is illustrated more particularly in FIG. 8. The program 98 knows that the previous transit time, $\Delta T$, was measured as a result of the previous transmitter firing. On the current transmitter firing, then the time gate 89 is conditioned to open just prior to (i.e. δt prior to) the expected transit time arrival of the ultrasonic energy. Thus time gate 89 is conditioned to pass ultrasonic energy signals from the transceiving transducer 86 only after a predetermined time period has elapsed from the transmitter firing. This prevents noise spikes or transceiver ring those such as illustrated in FIG. 8 from falsely triggering the detector comparator 90 upon arrival of the ultrasonic signal reflected from the opposite side of the sample. Thus random electrical noise or ringing effects from the firing of the transceiving transducer 86 as a transmitter are not detected by the comparator 90.

Upon opening of the time gate 89, the ultrasonic signals are supplied to the comparator 90 and compared with the reference voltage from DAC 99 which is determined as previously described. The arrival of the reflected ultrasonic signal causes an output pulse from the comparator 90 which is supplied to pulse generator 91. The pulse generator 91 then generates a stop signal which is supplied to counter 92. The counter 92 had previously been initialized by the generation of the sync pulse signal from sync pulse generator 82 to count output signals from the 20 megahertz clock oscillator 81. Thus, when counter 92 receives the stop signal from the pulse generator 91, the counter 92 contains a binary number or count which is directly related to the transit time of the ultrasonic energy through the sample 87 located in the autoclave unit. This number is strobed into a ΔT register 93 and is thereby made accessible to the measurement program 94.

The operation of control program 97, keyboard 96, measurement program 94 and display system 95 in FIG. 7 is directly analogous to the corresponding components previously discussed with respect to FIG. 1.

Thus, a second embodiment of the present invention is provided using a single transceiver transducer and a reflector rather than using separate transmitter and receiving transducers. Also, the action of the time gate 89 of FIG. 7 may be utilized to control false triggering of the detecting circuit due to noise events which could occur during the lapse of time between the transmitter firing and the receipt of the reflected signal at the transceiving transducer. This principle, of course, is also applicable to the system of FIG. 1, if desired.

In operation, the system monitors, in real time, the transit time of an ultrasonic signal through a cement sample for an interval of time which may range up to 1000 hours or more. A complete history is thus obtained of the compressive strength of the cement sample under controlled elevated temperature and pressure conditions, such as are present in a well borehole. The process of establishing the noise level and transit time through the cement sample is repeated each 10 seconds on each of the up to eight parallel autoclave channels of the present system. Thus, up to eight time histories of the development of strength in cement samples may be obtained.

The foregoing description may make other alternative arrangements according to the concepts of the invention apparent to those skilled in the art. It is therefore the aim of the appended claims to cover all such changes and modifications as fall within the true spirit and scope of the invention.

We claim:

1. A system for non-destructively measuring the compressive strength of a cement slurry sample comprising:
   means for housing a cement slurry sample and for controlling the pressure and temperature of the sample;
   means for generating an ultrasonic signal coupled to said sample;
   means for measuring the transit time of said ultrasonic signal through the sample and for generating a measurement signal representative thereof;
   means, responsive to said measurement signal, for generating according to a predetermined relationship relating transit time to compressive strength, a signal representative of the compressive strength of the sample; and
   means for recording said compressive strength signal.

2. The system of claim 1 and further including:
   control means for controlling said generating means and said measurement means to repetitively perform measurements of transit time and compressive strength; and
   means for recording said repetitive measurements of compressive strength as a function of time, thereby to provide a time history of the compressive strength of the cement sample.

3. The system of claim 2 and further including:
   means for comparing said repetitive measurement signals with an arbitrary comparison signal to determine when said measurement signal reaches the level of said comparison signal as a function of time; and
   means for recording the time at which said comparison signal level is met.

4. The system of claim 3 wherein said comparison signal comprises a signal representative of the initial set time of the cement slurry sample.

5. The system of claim 3 wherein said comparison signal comprises a signal representative of an arbitrary variable strength of the cement slurry sample.

6. The system of claim 1 wherein said means for measuring the transit time of said ultrasonic signal includes means for establishing a noise level characteristic of the measurement system and means for detecting when an ultrasonic signal transmitted through the sample exceeds said noise level by a predetermined amount.

7. The system of claim 6 and further including time gating means responsive to previous transit time measurements through a sample for establishing a time gate reception interval related to said previous transit time measurements for accepting the arrival of an ultrasonic signal transiting the sample.

8. The system of claim 1 wherein said means for generating an ultrasonic signal through the sample comprises piezoelectric transducer means coupled to said sample.

9. The system of claim 8 wherein said piezoelectric transducer means operated in a frequency range from 100 kilohertz to one megahertz.

10. The system of claim 9 wherein said piezoelectric transducer means operates at approximately 400 kilohertz frequency.

11. The system of claim 8 and further including a piezoelectric transducer means coupled to the sample on a side opposite said signal generating means, for receiving the ultrasonic signal transiting the sample.

12. The system of claim 8 wherein said piezoelectric transducer means further comprises a transceiving transducer means for both transmitting and receiving ultrasonic signals coupled to the sample.

13. The system of claim 12 and further including ultrasonic signal reflecting means coupled to the sample on a side opposite said transceiving transducer means.

14. A method for non-destructively measuring the compressive strength of a cement slurry sample, comprising the steps of:
    maintaining a cement slurry sample at controlled temperature and pressure;
    transmitting an ultrasonic signal through the sample;
    detecting said ultrasonic signal subsequent to its transiting the sample and measuring the time required for said signal to transit the sample;
    determining, according to a predetermined relationship relating transit time to compressive strength, the compressive strength of the sample; and
    recording the compressive strength of the sample.

15. The method of claim 14 wherein the steps are performed repetitively and the compressive strength of the sample is recorded as a function of time, thereby providing a time history of the compressive strength of the sample.

16. The method of claim 15 and further including the steps of:
    at each repetition of measurement of compressive strength of the sample, comparing the compressive strength with an arbitrary strength level and determining the time when the compressive strength reaches said arbitrary strength level; and
    recording the time at which the compressive strength reaches said arbitrary strength level.

17. The method of claim 16 wherein said arbitrary strength level represents the value of the initial set time of the sample.

18. The method of claim 16 wherein said arbitrary strength level represents an arbitrary variable strength of the cement slurry sample.

19. The method of claim 14 wherein the step of detecting said ultrasonic signal and measuring its transit time includes establishing a noise level characteristic of the measurement system and detecting when said ultrasonic signal exceed said noise level characteristic.

20. The method of claim 19 and further including the step of establishing a time region, based on previous measurements of the transit time of an ultrasonic signal across the sample, in which to detect the arrival of said ultrasonic signal.

21. The method of claim 14 wherein said transmitting and detecting steps are performed with separate piezoelectric transducer elements coupled to the sample.

22. The method of claim 14 wherein said transmitting and detecting steps are performed with a single piezoelectric transceiver transducer coupled to one side of the sample.

23. The method of claim 22 wherein a reflecting element is coupled to an opposite side of the sample.

24. The method of claim 14 wherein said steps are performed using an ultrasonic frequency in the range from 100 kilohertz to one megahertz.

25. The method of claim 14 wherein said steps are performed at a frequency of approximately 400 kilohertz.

* * * * *